United States Patent [19]

Ghanayem et al.

[11] 4,007,218

[45] Feb. 8, 1977

[54] ESTERIFICATION REACTION

[75] Inventors: Ibrahim Ghanayem, Downers Grove; Alvin E. Trevillyan, Naperville, both of Ill.

[73] Assignee: Standard Oil Company (Indiana), Chicago, Ill.

[22] Filed: July 31, 1975

[21] Appl. No.: 600,858

Related U.S. Application Data

[63] Continuation-in-part of Ser. No. 422,676, Dec. 7, 1973, abandoned.

[52] U.S. Cl. ............... 260/475 R; 260/475 B; 260/475 N; 260/475 PN; 260/479 S; 260/485 R; 260/485 N; 260/485 S; 260/31.8 R; 260/31.8 B
[51] Int. Cl.² ............... C07C 69/44; C07C 69/50; C07C 69/76; C07C 69/80
[58] Field of Search ........ 260/475 B, 485 S, 475 R, 260/485 R, 475 PN, 475 N, 485 L, 485 N, 479 S

[56] References Cited

UNITED STATES PATENTS 3,818,071  6/1974  Chilton ................. 260/475 B

FOREIGN PATENTS OR APPLICATIONS 1,945,359  3/1971  Germany ............... 260/475 B
45-35045  11/1970  Japan .................. 260/485 S

*Primary Examiner*—Jane S. Myers
*Attorney, Agent, or Firm*—William H. Magidson; Arthur G. Gilkes; William T. McClain

[57] ABSTRACT

Process of producing relatively pure esters, which comprises reacting a solution of organic acid compound in excess monohydroxy compound in the presence of a tetraalkyl titanate esterification catalyst to produce a monohydroxy solution of organic ester, treating the dissolved organic ester in the substantial absence of water at a temperature of at least 120° C. with solid alkaline earth metal oxide or hydroxide adding at least two mols of water per mol of alkaline earth metal at up to 100° C. and partitioning solid alkaline earth metal compound from the dissolved organic ester.

9 Claims, No Drawings

ESTERIFICATION REACTION

This application is a continuation-in-part of Ser. No. 422,676, filed Dec. 7, 1973, now abandoned.

This invention relates to the purification and/or isolation of esters. More particularly, this invention relates to the purification and/or isolation of esters which comprises reacting a monohydroxy compound and organic acid compound in the presence of a tetraalkyl titanate catalyst and treating said products with alkaline earth metal hydroxides or oxides in the substantial absence of water at a temperature of at least 120° C. and adding at least two moles water per mole of alkaline earth metal compound at up to 100° C.

Over 100 million pounds per year of synthetic organic esters are produced by the direct esterification of an organic acid compound and a monohydric alcohol. For example, esters of polycarboxylic acid compounds and monohydric alcohols are commonly used as plasticizers of resinous polymers of vinyl chloride in a concentration of 5 to 300 parts by weight per 100 parts by weight resinous polymr of vinyl chloride. These esters are generally produced by dissolving a suitable polycarboxylic acid or anhydride thereof in excess monohydric alcohol and carrying out the esterification in the presence of an esterification catalyst, such as para-toluenesulfonic acid or sulfuric acid. The catalyst, unreacted acid and partial esters are then removed from the alcoholic solution by neutralization with aqueous caustic followed by washing the neutralized ester with copious amounts of water. These isolation techniques require large amounts of water and produce waste water streams containing difficultly biodegradable organic materials. Further, hard to break emulsions are often formed during the washing steps, particularly when sulfuric acid is employed as the esterification catalyst. If the ester is improperly processed (all the alkali and residue are not removed), resinous polymers of vinyl chloride, plasticized with the ester, have inconsistent properties.

The aforesaid problems can be reduced by neutralizing the liquid esterification product (usually a solution of ester in excess alcohol) with moist alkaline earth metal oxides or hydroxides. Since the moist alkaline earth metal oxides and hydroxides are essentially solids, the alkaline earth metal oxides, hydroxides and salts of unreacted or partially reacted acid component can be partitioned from the dissolved esters. In this way, there is much less water consumed in the purification; there are no emulsions formed; and there is no need to be concerned with treating waste streams containing difficultly biodegradable materials. Although this technique has the aforesaid advantages, the esters are difficult to partition from the solid alkaline earth metal compound. Partitioning is slow and there is substantial occlusion of ester. For example, about 8 to 15% by weight of the ester is occluded by the solid alkaline earth metal compound when trimellitates are isolated by this technique.

The general object of this invention is to provide an improved method of producing esters and isolating and/or purifying the esterification products. Other objects appear hereinafter.

The objects of this invention can be attained by reacting monohydroxy compound with organic acid in the presence of a tetraalkyl titanate catalyst, treating the liquid with solid alkaline earth metal oxide or hydroxide in the substantial absence of unbound water at a temperature of at least 120° C. and adding two to twenty moles water per mole alkaline earth metal compound at up to 100° C. When a tetraalkyl titanate catalyst is used, it is much easier to separate the ester from alkaline earth metal compound and much less of the ester is occluded by alkaline earth metal compound. Separation is also facilitated by adding the alkaline earth metal at 120° C. or above and water at up to 100° C. If the water is added at over 100° C, there is a tendency for the water to flash off and there are relatively high levels of alkaline earth metal residues.

Suitable organic acid compounds (acids, or anhydrides) useful in this invention include polycarboxylic acid compounds, such as phthalic acid, phthalic anhydride, isophthalic acid, terephthalic acid, 2,5-dibromoterephthalic acid, trimellitic anhydride, trimellitic acid, adipic acid, adipic anhydride, sebacic acid, etc.

Suitable monohydroxy hydrocarbon compounds useful in this invention include alcohols containing from 1 to 24 carbon atoms such as methyl alcohol, ethyl alcohol, isopropyl alcohol, allyl alcohol, methallyl alcohol, n-butyl alcohol, n-hexyl alcohol, n-octyl alcohol, 2-ethylhexyl alcohol, decyl alcohol, tridecyl alcohol, stearyl alcohol, oleyl alcohol, tetracosyl alcohol; aromatic hydroxy compounds containing 6 to 18 carbon atoms, such as phenol, cresol, para-stearyl phenol, naphthol, etc. In general, the reaction vessel should contain from about 1 to 10 moles of monohydroxy compound per carboxyl equivalent in said organic acid compound in order to form a solution of ester in monohydroxy compound after the completion of the esterification reaction.

Suitable tetraalkyl titanate esterification catalysts useful in this invention have 1 to 18 carbon atoms in the alkyl groups and include tetrabutyl titanate, tetraethyl titanate, tetraisopropyl titanate, etc. In general, the catalyst comprises from about 0.05 to 5.0 parts by weight per 100 parts by weight of organic acid compound.

Suitable alkaline earth metal oxides and hydroxides include barium hydroxide, barium oxide, calcium hydroxide, calcium oxide, strontium hydroxide, strontium oxide, etc. In general, the alkaline earth metal should be used in a concentration from about 0.1 to 35 equivalents per equivalent of acid material in the reaction product (unreacted acid, partial esters, etc.), preferably 1 to 25 equivalents.

In somewhat greater detail this invention comprises dissolving polycarboxylic acid compound in from about 1 to 10 moles of monohydroxy substituted hydrocarbon compound per carboxyl equivalent in said organic acid compound. If desired, a diluent such as a xylene or toluene may also be added to aid in the entrainment of water of esterification and to promote the esterification reaction. Either before or after the polycarboxylic acid is dissolved in the monohydroxy compound, a suitable concentration of tetraalkyl titanate catalyst is added to the reactor.

The esterification mixture is then heated to a temperature of 120° to 250° C. either under pressure or under suitable reflux conditions for a period of time to complete the esterification. After the esterification is completed, the solution of ester in monohydroxy compound and/or diluent is treated at 120° C. or higher with the alkaline earth metal oxide or hydroxide compound and cooled to 100° C. or lower prior to the addition of water. The alkaline earth metal compound can be added all at once or in increments. Likewise the water can be added in one or several increments.

The preferred method of treating the ester composition comprises adding an alcoholic suspension of alkaline earth metal hydroxide (or hydrated oxide) in the substantial absence of unbound water to the ester composition at 120° C. or higher and subsequently adding 2 to 20 moles. of water per mole of alkaline earth metal hydroxide while maintaining the ester below 100° C., preferably 60° to 95° C. The alkaline earth metal hydroxide is preferably added at 120° C. or higher to obtain rapid reduction in acidic components and titanium content. Other things being equal, it takes twice as long to obtain the same degree of treatment at temperatures under 100° C., e.g. 3 to 4 hours vs. 1½ to 2 hours. If unbound water is added at temperatures over 100° C. with alkaline earth metal compound, the unbound water tends to flash off; there is a tendency for saponification of ester groups and a slight decrease in rate of filtration. However, the additional water, when added to the ester composition at below 100° C, assures substantially complete scavenging of titanium residues, alkaline earth metal residues and acidic components (free acid and partial esters).

The ester is then separated from the suspended alkaline earth metal compound by partitioning, such as by filtration or by centrifugation. As indicated above, the esters produced using the tetraalkyl titanate can be partitioned much more rapidly than esters produced using sulfate or sulfonate catalysts. For example, other things being equal the filtration rate of trimellitates is at least 4 to 10 times faster using the catalysts of this invention.

Any residual alkaline earth metal compound in the ester composition can be removed by extracting the ester with water thereby dissolving alkaline earth metal hydroxide. However, this aqueous extraction is usually unnecessary. The excess alcohol and/or diluent can then be removed from the ester by distillation and recycled to the esterification unit. Alternatively, excess alcohol and diluent can be removed from the ester by distillation before the alkaline earth metal compound is partitioned from the ester.

Although approximately 8 to 15% by weight of the ester is usually occluded on the partitioned alkaline earth metal compound when sulfate and sulfonate catalysts are used, about 1 to 2% ester is occluded when titanate catalyst is used. The ester can be recovered in various ways from alkaline earth metal compound. For example, the ester can be freed from the alkaline earth metal compound by washing with the same alcohol used in the esterification reaction. This second crop alcoholic ester composition can be added to the first crop alcoholic ester composition or recycled to the esterification unit. If the second crop alcoholic ester composition is combined with the first crop, the second crop ester or the combined esters should be extracted with water to remove contaminating alkaline earth metal compounds. If the second crop is returned to the esterification unit, the alkaline earth metal compound can be removed by forming the sulfate salt with sulfuric acid and partitioning insoluble alkaline earth metal sulfate. Loss of ester can also be minimized by using the alkaline earth metal hydroxide containing occluded ester to neutralize the next batch of ester.

The following examples are merely illustrative.

EXAMPLE 1

A series of tri(2-ethylhexyl) trimellitate esters were prepared in the following manner:

Five moles trimellitic anhydride, 18 moles 2-ethylbexanol and 8.5 g. of tetrabutyl titanate were placed in a 4-neck 3-liter flask fitter with a mechanical stirrer, nitrogen sparge tube, thermometer, heating mantle, Dean-Stark water trap and a condenser. The reactants were stirred and heated to 210° C. for approximately 2½ to 3 hours until the esterification was completed and the reaction mixture had an acid number less than 0.5 mg KOH/g. After the reaction mixture was cooled to about 145 to 160° C., 20 g. calcium hydroxide in 50 ml 2-ethylhexanol was added to the reaction mixture and stirred for about 2 hours at about 145° to 160° C. The mixture was cooled to 90° C. and 40 g. of water were added while maintaining the composition at 90° C. with stirring for an additional 0.5 hour. Forty g. of Celite (Hyflow Super-Celite filter aid) was added and stirred for 5 minutes prior to filtration through a sparkler filter precoated with 6 g. of Celite. The ester was stripped of excess alcohol and residual water at 160° C. and 75 mm mercury using a steam sparge. The results are set forth below in Table I. Another run using sulfuric acid as a catalyst and a reaction temperture of 160° C. was employed as a control.

Table I

| Catalyst | Lime Treatment Temperature | Filtration Rate* | 500 ml** | Cake wt. | % Ester Lost on cake |
|---|---|---|---|---|---|
| Titanate | 160° C. | 718 ml/min | 0.25 min. | 98 g. | — |
| Titanate | 160° C. | 400 ml/min | 0.5 min. | 111 g. | 1.4 |
| Titanate | 145° C. | 158 ml/min | 1.0 min. | 134 g. | 2.1 |
| H₂SO₄ | 160° C. | 45 ml/min | 10 min | — | 8 to 15*** |

*Stands for average ml per minute collected in first 5 minutes
**Stands for minutes necessary to collect 500 ml.
***Typical values from 1 to 5 mole esterifications with sulfuric acid.

The above data indicates that the use of titanate catalysts result in better filtration rates and less occlusion of ester on the insoluble alkaline earth metal compounds.

Essentially the same results are obtained using equal moles of tetraisopropyl titanate in place of tetrabutyl titanate.

EXAMPLE 2

The process described in Example 1 was repeated using 1 mole isophthalic acid, 2.2 moles 2-ethylhexanol and 2 g. of tetraisopropyl titanate catalyst. The reaction was heated to 203° C. and maintained for 4 hours until the reaction mixture had an acid number of 1.1 mg KOH/g. A slurry of 12 g. calcium hydroxide in 40 ml 2-ethylhexanol was added to the reaction, the mixture stirred at 160° C. for 15 minutes, cooled to 90° C., 7 g. of water added and the mixture maintained at 90° C. for an additional 15 minutes prior to filtration in the manner described in Example 1. Filtration rate was 85 ml/minutes.

We claim:

1. The process of producing relatively pure esters, which comprises reacting a solution of at least one organic polycarboxylic acid compound selected from the group consisting of phthalic acid, phthalic anhydride, isophthalic acid, terephthalic acid, 2,5-dibromoterephthalic acid, trimellitic anhydride, trimellitic acid, adipic acid, adipic anhydride, and sebacic acid in the presence of a tetraalkyl titanate esterification catalyst in excess monohydroxy hydrocarbon compounds selected from the group consisting of alcohols containing from 1 to 24 carbon atoms and aromatic hydroxy compounds containing 6 to 18 carbon atoms to produce a monohydroxy solution of organic ester, treating the dissolved organic ester in the substantial absence of unbound water at a temperature of at least 120° C with at least one solid alkaline earth metal compound selected from the group consisting of alkaline earth metal oxide and alkaline earth metal hydroxide, adding subsequently two to twenty mols of water per mol of alkaline earth compound to the dissolved ester at up to 100° C and partitioning solid alkaline earth metal compound from the dissolved organic ester, wherein the concentration of alkaline earth metal compound is 0.1 to 35 equivalents per equivalent of acid material in the monohydroxy solution of organic ester.

2. The process of claim 1, wherein said tetraalkyl titanate is selected from the group consisting of tetraisopropyl titanate and tetrabutyl titanate.

3. The process of claim 2, wherein the alkaline earth metal compound is an alkaline earth metal hydroxide.

4. The process of claim 3 wherein said alkaline earth metal hydroxide is calcium hydroxide.

5. The process of claim 3, wherein said alkaline earth metal hydroxide is a hydrated alkaline earth metal oxide.

6. The process of claim 5, wherein said alkaline earth metal oxide is calcium oxide.

7. The process of claim 1, wherein said polycarboxylic acid compound is a trimellitic acid compound.

8. The process of claim 7, wherein said monohydroxy compound is used in a concentration of from about 1 to 10 moles per equivalent of polycarboxylic acid compound.

9. The process of claim 8, wherein said monohydroxy compound is 2-ethylhexanol.

* * * * *